United States Patent
Bringley et al.

(10) Patent No.: US 7,357,979 B2
(45) Date of Patent: Apr. 15, 2008

(54) COMPOSITION OF MATTER COMPRISING POLYMER AND DERIVATIZED NANOPARTICLES

(75) Inventors: Joseph F. Bringley, Rochester, NY (US); Richard W. Wien, Pittsford, NY (US); David L. Patton, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 334 days.

(21) Appl. No.: 10/822,929

(22) Filed: Apr. 13, 2004

(65) Prior Publication Data

US 2005/0228099 A1    Oct. 13, 2005

(51) Int. Cl.
    *B32B 5/16*    (2006.01)
(52) U.S. Cl. ............... 428/323; 428/328; 428/331
(58) Field of Classification Search ............ None
    See application file for complete search history.

(56) References Cited

U.S. PATENT DOCUMENTS

| | | | |
|---|---|---|---|
| 4,530,963 A | 7/1985 | DeVoe et al. | |
| 4,701,500 A | 10/1987 | Porath | |
| 5,217,998 A | 6/1993 | Hedlund et al. | |
| 5,760,126 A | 6/1998 | Engle et al. | |
| 5,854,303 A | 12/1998 | Powell et al. | |
| 6,156,234 A | 12/2000 | Briscoe et al. | |
| 6,489,499 B1 | 12/2002 | King et al. | |
| 6,830,694 B2 * | 12/2004 | Schiestel et al. ............ 210/660 |
| 2003/0078209 A1 | 4/2003 | Schmidt | |

FOREIGN PATENT DOCUMENTS

| | | |
|---|---|---|
| JP | 08218041 | 12/1996 |
| WO | 98/51435 | 11/1998 |
| WO | 03/038842 | 5/2003 |
| WO | 03/089113 | 10/2003 |

OTHER PUBLICATIONS

"Direct Synthesis of Metal-Chelating Mesoporous Silica: Effects of Added Organosilanes on Silicate Formation and Adsorption Properties," Markowitz et al. (J. Phys. Chem B. 104, 10820 (2000)).

"Novel Sol-Gel-Derived Material for Separation and Optical Sensing of Metal Ions: Propyl-ethylenediamine Triacetate Functionalized Silica," Tien et al., (Chem. Mater. 11,2141 (1999)).

* cited by examiner

*Primary Examiner*—Monique R. Jackson
(74) *Attorney, Agent, or Firm*—Andrew J. Anderson; Sarah Meeks-Roberts

(57) ABSTRACT

This invention is related to a composition of matter useful for sequestering target metal-ions from an environment, said composition comprising a polymer and derivatized nanoparticles comprising inorganic nanoparticles having an attached metal-ion sequestraint, wherein said inorganic nanoparticles have an average particle size of less than 200 nm and the derivatized nanoparticles have a stability constant greater than $10^{10}$ with iron (III).

28 Claims, No Drawings

COMPOSITION OF MATTER COMPRISING POLYMER AND DERIVATIZED NANOPARTICLES

FIELD OF THE INVENTION

The present invention relates to a composition of matter useful for sequestering target metal-ions from a contacting environment, comprising a polymer and derivatized nanoparticles having a high-affinity and high capacity for metal-ions. The invention also relates to articles useful for sequestering target metal-ions from a surrounding environment, and able to prevent microbial contamination.

BACKGROUND OF THE INVENTION

Numerous materials and methods have been developed for providing antimicrobial properties to medical items, consumer articles and food packaging. Nearly all of the methods thus far developed rely on the release of bacteriocides or bacteriostats to kill unwanted microbes such as bacteria, viruses, yeast, etc. There is a general problem with this approach in that the released chemicals can be harmful to the user of said items, or may leach into aquatic or surrounding environments. Materials and methods which are cleaner and safer are needed to prevent microbial contamination and infectious disease.

Small concentrations of metal-ions may play an important role in biological processes. For example, Mn, Fe, Ca, Zn, Cu and Al are essential bio-metals, and are required for most, if not all, living systems. Metal-ions play a crucial role in oxygen transport in living systems, and regulate the function of genes and replication in many cellular systems. Calcium is an important structural element in the formation of bones and other hard tissues. Mn, Cu and Fe are involved in metabolism and enzymatic processes. At high concentrations, metals may become toxic to living systems and the organism may experience disease or illness if the level cannot be controlled. As a result, the availability and concentrations of metal-ions in biological environments is a major factor in determining the abundance, growth-rate and health of plant, animal and micro-organism populations.

It has been recognized that iron is an essential biological element, and that all living organisms require iron for survival and replication. Although the occurrence and concentration of iron is relatively high on the earth's surface, the availability of "free" iron is severely limited by the extreme insolubility of iron in aqueous environments. As a result, many organisms have developed complex methods of procuring "free" iron for survival and replication. Controlling the concentration of "free" iron in any biological system can, therefore, allow one to control the growth rates and abundance of micro-organisms. Such control can be of great use for treating sickness and disease, inhibiting bacterial growth, treating wounds, and providing for the general health of plant, animal, micro-organism and human populations. Indeed, iron "chelating" or "sequestering" drugs are used to treat iron deficiency in plants; and are used to treat diseases such as Cooley's anemia (thalassemia), sickle-cell anemia, and iron overload diseases in humans.

Metal-ions may also exist as contaminants in environments such as drinking water, beverages, food, industrial effluents and public waste waters, and radioactive waste. Methods and materials for removing such contaminants are important for cleaning the environment(s) and providing for the safety of the general public.

U.S. Pat. No. 5,217,998 to Hedlund et al. describes a method for scavenging free iron or aluminum in fluids such as physiological fluids by providing in such fluids a soluble polymer substrate having a chelator immobilized thereon. A composition is described which comprises a water-soluble conjugate comprising a pharmaceutically acceptable water-soluble polysaccharide covalently bonded to deferoxamine, a known iron chelator. The conjugate is said to be capable of reducing iron concentrations in body fluids in vivo.

U.S. Pat. No. 6,156,334 to Meyer-Ingold et al. describes novel wound coverings which can remove interfering factors (such as iron ions) from the wound fluid of chronic wounds. The wound coverings may comprise iron chelators covalently bonded to a substrate such as cloth or cotton bandages. U.S. patent application US 2003/0078209 A1 to Schmidt et al. describes solid porous compositions, substantially insoluble in water, comprising at least 25% by weight of an oxidized cellulose and having a significant capacity to bind iron. The invention also provides a method of sequestering dissolved iron from aqueous environments. The compositions may be used for the prevention or treatment of infections by bacteria or yeast.

U.S. Pat. No. 6,489,499 B1 to King et al. describes novel compounds comprising siloxane modified carboxylic acid substituted amines. The compounds of the invention are said to provide many of the desirable properties of ethylene diammine tetraacetic acid and its salts in a stationary phase. The stationary substrate may comprise silicate glass, silica, alumina, inorganic clays, etc. Markowitz et al. (J. Phys. Chem. B. 104, 10820 (2000)) describes metal chelating agents, such as carboxylic acid substituted amines, covalently bound to mesoporous silica. Tien (Chem. Mater. 11, 2141(1999)) describes silica gels functionalized with carboxylic acid substituted amines, the functionalization of which was accomplished using siloxane modified carboxylic acid substituted amines. The usefulness of the material "as a stationary phase for chromatographic separation of metal-ions" was demonstrated.

The materials and methods described above, while capable of sequestering metal-ions, are limited in their capacity for several reasons. First, because the particle size of the substrate or of the stationary phase is large (>1 micron), only a limited amount of metal-ion sequestering agent can be applied to the surfaces of the substrate. This is especially true if the substrate or stationary phase contains no internal surfaces (i.e., are not porous). Metal-ion sequestering agent in excess of the available surface area, cannot be bound to the substrates surfaces, and therefore, will not be effective in sequestering or separating metal-ions from the contacting environment. Because sequestering media prepared as in the prior art have limited capacity, large amounts of material are required to effectively remove metal-ions and their application can be costly. Additionally large particles strongly scatter light, and cannot be applied to transparent or colored surfaces or articles without rendering the surface or article opaque or white. This alters significantly the appearance of the article containing the sequestering agent and precludes the use of large particles in many applications.

Materials are needed that are able to target and remove specific metal-ions, while leaving intact the concentrations of beneficial metal-ions. Furthermore, materials are needed that have a high capacity for metal-ions and that provide for the efficient removal of metal-ions in a cost effective manner. Materials and methods are needed for sequestering metal-ions even in extremely low concentrations and removing metal-ion contaminants to levels below 100 parts per billion (ppb) and still further below 10 ppb. Materials and methods are needed for applying immobilized metal-ion sequestraints to numerous items and articles without significantly changing their color or appearance.

SUMMARY OF THE INVENTION

This invention provides a composition of matter useful for sequestering target metal-ions from an environment, said composition comprising a polymer and derivatized nanoparticles comprising inorganic nanoparticles having an attached metal-ion sequestraint, wherein said inorganic nanoparticles have an average particle size of less than 200 nm and the derivatized nanoparticles have a stability constant greater than $10^{10}$ with iron (III). This invention further provides an article comprising a polymeric layer containing said derivatized nanoparticles, capable of sequestering metal-ions from a surrounding environment. The invention further provides an article having as its outer-most layer a barrier layer; and a polymeric layer comprising said derivatized nanoparticles between the surface of the article and the barrier layer; wherein the barrier layer does not contain the derivatized nanoparticles and is impenetrable to microbes such as bacteria, viruses and fungi.

The derivatized nanoparticles used in the invention are able to target and remove specific metal-ions, while leaving intact the concentrations of beneficial metal-ions. Furthermore, they have a very high capacity for metal-ions and provide for the efficient removal of metal-ions in a cost effective manner. They can sequester metal-ions even in extremely low concentrations and remove metal-ion contaminants to levels below 100 parts per billion (ppb) and still further below 10 ppb. They can be utilized in numerous items and articles without significantly changing their color or appearance and they are easy to apply. The nanoparticles can be utilized to remove metal-ions which are themselves contaminants, or they can be used to remove metal-ions which are nutrients for biological contaminants. The nanoparticles do not release chemicals that can be harmful to humans or that may leach into aquatic or surrounding environments. Such materials and methods are cleaner and safer in preventing microbial contamination and infectious disease. The use of the polymer aids in coating an article comprising the nanoparticles. It may further control the availability of the sequestraint to the target metal ions. The barrier layer may also control the availability of the sequestraint to the target metal-ions and it may prevent the polymeric layer from being contaminated by microbes or other contaminants. The barrier layer may provide several other functions including improving the physical strength and toughness of the article and resistance to scratching, marring, cracking, etc.

DETAILED DESCRIPTION OF THE INVENTION

The composition of matter of the invention is useful for removing or sequestering target metal-ions from an environment. In many instances, it is necessary to remove metal-ions from environments such as drinking water, food, biological fluids, industrial effluents and public waste water, and radioactive waste. The composition of matter of the present invention may be applied to articles such as filters, sponges, membranes, textiles, fibres, plastics, metals, paper and other materials used in the construction of articles. Articles containing the composition of matter of the invention are placed in contact with the environment in an amount sufficient to bind the target metal-ion(s), and are then removed or separated from the environment, leaving the environment substantially free of the target metal-ion(s). Alternatively, the inventive composition may be used to recover metal-ions such as precious metals, for example gold and silver, from liquid environments.

In a particular application of the invention, the composition of matter may be applied to the surfaces of consumer items such as plastic wraps, papers, cellophane and polymer films, glass and metal containers and other packaging materials, especially food packaging materials. The composition of matter of the invention may also be applied to medical items such as bandages, gauze, cotton and personal hygiene items such as diapers, bandaids, and other items which come into contact with biological and body fluids. The composition of matter of the present invention may be applied to such items such that it is transparent and un-noticeable to the user of the article. The composition of matter of the invention, and articles comprising the composition of matter of the invention are able to remove or sequester metal-ions such as Zn, Cu and Fe which are essential for biological growth, and thus may inhibit the growth of harmful microorganisms such as bacteria, viruses, and fungi in the environment they contact. The invention "starves" the microorganisms of minute quantities of essential nutrients and hence limits their growth and reduces the risk due to bacterial, viral and other infectious diseases.

The invention provides a composition of matter useful for sequestering target metal-ions from an environment, said composition comprising a polymer and derivatized nanoparticles comprising inorganic nanoparticles having an attached metal-ion sequestraint, wherein said inorganic nanoparticles have an average particle size of less than 200 nm and the derivatized nanoparticles have a stability constant greater than $10^{10}$ with iron (III). The term "environment" refers to environments that articles or items comprising the inventive composition may come in contact with, and include aqueous and non-aqueous environments containing metal-ion contaminants. It is preferred that the environment is a liquid medium and that the polymer of the inventive composition is permeable to the liquid medium. This is preferred because permeability facilitates the contact of the contaminant metal-ions with the derivatized nanoparticles, which, in turn, facilitates the sequestration of the metal-ions at the nanoparticle surfaces. Aqueous environments contemplated as applicable to the invention include water, waste water, industrial effluents and radioactive waste, and consumable environments such as drinking water, beverages and food, consumer household environments such as cosmetics, shampoos, tooth paste, etc. Typical environments encountered also include biological and body, fluids.

It is preferred that the environment is an aqueous medium and that the polymer is permeable to said aqueous medium. It is important that the polymer is permeable to the aqueous media because it facilitates the contact of the contaminant metal-ions with the derivatized nanoparticles, which, in turn, facilitates the sequestration of the metal-ions at the nanoparticle surfaces. A measure of the permeability of various polymeric addenda to water is given by the permeability coefficient, P which is given by $$P = (\text{quantity of permeate})(\text{film thickness})/[\text{area} \times \text{time} \times (\text{pressure drop across the film})]$$

Permeability coefficients and diffusion data of water for various polymers are discussed by J. Comyn, in *Polymer Permeability*, Elsevier, N.Y., 1985 and in "Permeability and Other Film Properties Of Plastics and Elastomers", Plastics Design Library, NY, 1995. The higher the permeability coefficient, the greater the water permeability of the polymeric media. The permeability coefficient of a particular polymer may vary depending upon the density, crystallinity, molecular weight, degree of cross-linking, and the presence of addenda such as coating-aids, plasticizers, etc. It is preferred that the polymer has a water permeability of greater than $1000[(cm^3 \ cm)/(cm^2 \ sec/Pa)] \times 10^{13}$.

It is further preferred that the polymer has a water permeability of greater than $5000[(cm^3 \ cm)/(cm^2 \ sec/Pa)] \times 10^{13}$. Preferred polymers for practice of the invention are polyvinyl alcohol, cellophane, water-based polyurethanes, polyester, nylon, high nitrile resins, polyethylene-polyvinyl alcohol copolymer, polystyrene, ethyl cellulose, cellulose acetate, cellulose nitrate, aqueous latexes, polyacrylic acid, polystyrene sulfonate, polyamide, polymethacrylate, polyethylene terephthalate, polystyrene, polyethylene, polypropylene or polyacrylonitrile. It is preferred that the derivatized nanoparticles are 0.1 to 50.0% by weight of the polymer, and more preferably 1% to 10% by weight of the polymer.

It is preferred that the nanoparticles have an average particle size of less than 100 nm. It is further preferred that the nanoparticles have an average size of less than 50 nm, and most preferably less than 20 nm. Preferably greater than 95% by weight of the nanoparticles are less than 200 nm, more preferably less than 100 nm, and most preferably less than 50 nm. This is preferred because as the particle size becomes smaller, the particles scatter visible-light less strongly. Therefore, the composition of matter can be applied to clear, transparent surfaces without causing a hazy or a cloudy appearance at the surface. This allows the particles of the present invention to be applied to consumer items, or other items without changing the appearance of that item. It is preferred that the nanoparticles have a very high surface area, since this provides more surface with which to covalently bind the metal-ion sequestraint, thus improving the capacity of the derivatized nanoparticles for binding metal-ions. It is preferred that the nanoparticles have a specific surface area of greater than 10 $m^2/g$, preferably greater than 100 $m^2/g$, more preferably greater than 200 $m^2/g$, and most preferably greater than 300 $m^2/g$. For applications of the invention in which the concentrations of contaminant or targeted metal-ions in the environment is high, it is preferred that the nanoparticles have a particle size of less than 20 nm and a surface area of greater than 300 $m^2/g$.

The inorganic nanoparticles of the invention preferably comprise silica oxides, alumina oxides, boehmites, titanium oxides, zinc oxides, tin oxides, zirconium oxides, yttrium oxides, hafnium oxides, clays or alumina silicates, and more preferably comprise silicon dioxide, alumina oxide, clays or boehmite. The nanoparticles may comprise a combination or mixture of the above materials. The term "clay" is used to describe silicates and alumino-silicates, and derivatives thereof. Some examples of clays which are commercially available are montmorrillonite, hectorite, and synthetic derivatives such as laponite. Other examples include hydrotalcites, zeolites, alumino-silicates, and metal (oxy)hydroxides given by the general formula, $M_aO_b(OH)_c$, where M is a metal-ion and a, b and c are integers. It is preferred that the nanoparticles of the invention, before being derivatized, have a positive zeta potential, preferably greater than 25 mV.

The derivatized nanoparticles of the invention have an attached metal-ion sequestraint and have a high-affinity for metal-ions and are able to sequester or remove metal-ions from aqueous or biological environments. Preferably said metal-ion sequestraint has a high-affinity for iron, copper, zinc, aluminum or heavy metals. The term heavy metals refers to metals having an atomic weight greater than about 100 g/mol, such as Ag, Au, Tl, Pb, Cd, and also lanthanides such as La, Ce, Sm, Eu, and Gd, and radioactive metals such as Th, U and Pu. It is also preferred that the derivatized particles have a high-affinity for biologically significant metal-ions, such as, Zn, Cu, Mn and Fe.

A measure of the "affinity" of metal-ion sequestraints for various metal-ions is given by the stability constant (also often referred to as critical stability constants, complex formation constants, equilibrium constants, or formation constants) of that sequestraint for a given metal-ion. Stability constants are discussed at length in "Critical Stability Constants", A. E. Martell and R. M. Smith, Vols. 1-4, Plenum, N.Y. (1977), "Inorganic Chemistry in Biology and Medicine", Chapter 17, ACS Symposium Series, Washington, D.C. (1980), and by R. D. Hancock and A. E. Martell, Chem. Rev. vol. 89, p. 1875-1914 (1989). The ability of a specific molecule or ligand to sequester a metal-ion may depend also upon the pH, the concentrations of interfering ions, and the rate of complex formation (kinetics). Generally, however, the greater the stability constant, the greater the binding affinity for that particular metal-ion. Often the stability constants are expressed as the natural logarithm of the stability constant. Herein the stability constant for the reaction of a metal-ion (M) and a sequestraint or ligand (L) is defined as follows:

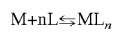

where the stability constant is $\beta_n=[ML_n]/[M][L]^n$, wherein $[ML_n]$ is the concentration of "complexed" metal-ion, [M] is the concentration of free (uncomplexed) metal-ion and [L] is the concentration of free ligand. The log of the stability constant is log $\beta_n$, and n is the number of ligands which coordinate with the metal. It follows from the above equation that if $\beta_n$ is very large, the concentration of "free" metal-ion will be very low. Ligands with a high stability constant (or affinity) generally have a stability constant greater than $10^{10}$ or a log stability constant greater than 10 for the target metal. Preferably the ligands have a stability constant greater than $10^{15}$ for the target metal-ion. Table 1 lists common ligands (or sequestraints) and the natural logarithm of their stability constants (log $\beta_n$) for selected metal-ions.

TABLE 1

Common ligands (or sequestraints) and the natural logarithm of their stability constants (log $\beta_n$) for selected metal-ions.

| Ligand | Ca | Mg | Cu(II) | Fe(III) | Al | Ag | Zn |
|---|---|---|---|---|---|---|---|
| alpha-amino carboxylates | | | | | | | |
| EDTA | 10.6 | 8.8 | 18.7 | 25.1 | | 7.2 | 16.4 |
| DTPA | 10.8 | 9.3 | 21.4 | 28.0 | 18.7 | 8.1 | 15.1 |
| CDTA | 13.2 | | 21.9 | 30.0 | | | |
| NTA | | | | 24.3 | | | |
| DPTA | 6.7 | 5.3 | 17.2 | 20.1 | 18.7 | 5.3 | |
| PDTA | 7.3 | | 18.8 | | | | 15.2 |
| citric Acid | 3.50 | 3.37 | 5.9 | 11.5 | 7.98 | 9.9 | |
| salicylic acid | | | | 35.3 | | | |
| Hydroxamates | | | | | | | |
| Desferrioxamine B | | | | 30.6 | | | |
| acetohydroxamic acid | | | | 28 | | | |

TABLE 1-continued

Common ligands (or sequestrants) and the natural logarithm
of their stability constants (log $\beta_n$) for selected metal-ions.

| Ligand | Ca | Mg | Cu(II) | Fe(III) | Al | Ag | Zn |
|---|---|---|---|---|---|---|---|
| Catechols | | | | | | | |
| 1,8-dihydroxy naphthalene 3,6 sulfonic acid | | | | 37 | | | |
| MECAMS | | | | 44 | | | |
| 4-LICAMS | | | | 27.4 | | | |
| 3,4-LICAMS | 16.2 | | | 43 | | | |
| 8-hydroxyquinoline | | | | 36.9 | | | |
| disulfocatechol | 5.8 | 6.9 | 14.3 | 20.4 | 16.6 | | |

EDTA is ethylenediamine tetraacetic acid and salts thereof,
DTPA is diethylenetriaminepentaacetic acid and salts thereof,
DPTA is Hydroxylpropylenediaminetetraacetic acid and salts thereof,
NTA is nitrilotriacetic acid and salts thereof,
CDTA is 1,2-cyclohexanediamine tetraacetic acid and salts thereof,
PDTA is propylenediammine tetraacetic acid and salts thereof.
Desferrioxamine B is a commercially available iron chelating drug, desferal ®.
MECAMS, 4-LICAMS and 3,4-LICAMS are described by Raymond et al. in "Inorganic Chemistry in Biology and Medicine", Chapter 18, ACS Symposium Series, Washington, D.C. (1980). Log stability constants are from "Critical Stability Constants", A. E. Martell and R. M. Smith, Vols. 1-4, Plenum Press, NY (1977); "Inorganic Chemistry in Biology and Medicine", Chapter 17, ACS Symposium Series, Washington, D.C. (1980); R. D. Hancock and A. F. Martell, Chem. Rev. vol. 89, p. 1875-1914 (1989) and "Stability Constants of Metal-icon Complexes", The Chemical Society, London, 1964.

In many instances, a disease may be associated with a particular metal-ion, either due to a deficiency of this metal-ion, or due to an overload (overdose) of this metal-ion. In such cases it may be desirable to synthesize a derivatized nanoparticle with a very high specificity or selectivity for a given metal-ion. Derivatized nanoparticles of this nature may be used to control the concentration of the target metal-ion and thus treat the disease or illness associated with this metal-ion. One skilled in the art may prepare such derivatized nanoparticles by selecting a metal-ion sequestraint having a high specificity for the target metal-ion. The specificity of a metal-ion sequestraint for a target metal-ion is given by the difference between the log of the stability constant for the target metal-ion, and the log of the stability constant for the interfering metal-ions. For example, if a treatment required the removal of Fe(III), but it was necessary to leave the Ca-concentration unaltered, then from Table 1, DTPA would be a suitable choice since the difference between the log stability constants 28−10.8=17.2, is very large. 3,4-LICAMS would be a still more suitable choice since the difference between the log stability constants 43−16.2=26.8, is the largest in Table 1.

It is preferred that the derivatized nanoparticles have a high stability constant for the target metal-ion(s). The stability constant for the derivatized nanoparticle will largely be determined by the stability constant for the attached metal-ion sequestraint. However, The stability constant for the derivatized nanoparticles may vary somewhat from that of the attached metal-ion sequestraint. Generally, it is anticipated that metal-ion sequestraints with high stability constants will give derivatized nanoparticles with high stability constants. For a particular application, it may be desirable to have a derivatized nanoparticle with a high selectivity for a particular metal-ion. In most cases, the derivatized nanoparticle will have a high selectivity for a particular metal-ion if the stability constant for that metal-ion is about $10^6$ greater than for other ions present in the system.

It is further preferred that said metal-ion sequestraint has a high-affinity for iron, and in particular iron(III). It is preferred that the stability constant of the sequestraint for iron(III) be greater than $10^{10}$. It is still further preferred that the metal-ion sequestraint has a stability constant for iron greater than $10^{20}$. It is still further preferred that the metal-ion sequestraint has a stability constant for iron greater than $10^{30}$.

Metal-ion sequestraints may be chosen from various organic molecules. Such molecules having the ability to form complexes with metal-ions are often referred to as "chelators", "complexing agents", and "ligands". Certain types of organic functional groups are known to be strong "chelators" or sequestraints of metal-ions. It is preferred that the sequestraints of the invention contain alpha-amino carboxylates, hydroxamates, or catechol, functional groups. Hydroxamates, or catechol, functional groups are preferred. Alpha-amino carboxylates have the general formula:

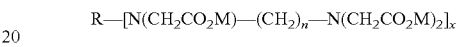

where R is an organic group such as an alkyl or aryl group; M is H, or an alkali or alkaline earth metal such as Na, K, Ca or Mg, or Zn; n is an integer from 1 to 6; and x is an integer from 1 to 3. Examples of metal-ion sequestraints containing alpha-amino carboxylate functional groups include ethylenediaminetetraacetic acid (EDTA), ethylenediaminetetraacetic acid disodium salt, diethylenetriaminepentaacetic acid (DTPA), Hydroxylpropylenediaminetetraacetic acid (DPTA), nitrilotriacetic acid, triethylenetetraaminehexaacetic acid, N,N'-bis(o-hydroxybenzyl)ethylenediamine-N,N' diacteic acid, and ethylenebis-N,N'-(2-o-hydroxyphenyl)glycine.

Hydroxamates (or often called hydroxamic acids) have the general formula:

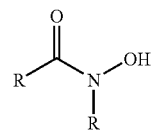

where R is an organic group such as an alkyl or aryl group. Examples of metal-ion sequestraints containing hydroxamate functional groups include acetohydroxamic acid, and desferroxamine B, the iron chelating drug desferal.

Catechols have the general formula:

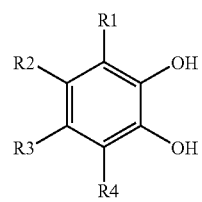

Where R1, R2, R3 and R4 may be H, an organic group such as an alkyl or aryl group, or a carboxylate or sulfonate group. Examples of metal-ion sequestraints containing catechol functional groups include catechol, disulfocatechol, dimethyl-2,3-dihydroxybenzamide, mesitylene catecholamide (MECAM) and derivatives thereof, 1,8-dihydroxynaphthalene-3,6-sulfonic acid, and 2,3-dihydroxynaphthalene-6-sulfonic acid.

In a preferred embodiment of the invention, the metal-ion sequestraint is attached to the nanoparticle, by reaction of the nanoparticle with a metal alkoxide intermediate of the sequestraint having the general formula:

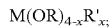
$$M(OR)_{4-x}R'_{x;}$$

wherein M is silicon, titanium, aluminum, tin, or germanium;

x is an integer from 1 to 3;

R is an organic group; and

R' is an organic group containing an alpha-amino carboxylate, a hydroxamate, or a catechol, functional group.

In a particularly preferred embodiment the metal-ion sequestraint is attached to the nanoparticle by reaction of the nanoparticle with a silicon alkoxide intermediate having the general formula:

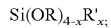
$$Si(OR)_{4-x}R'_{x;}$$

wherein x is an integer from 1 to 3;

R is an alkyl group; and

R' is an organic group containing an alpha amino carboxylate, a hydroxamate, or a catechol. The —OR-group attaches the silicon alkoxide to the core particle surface via a hydrolysis reaction with the surface of the particles. Materials suitable for practice of the invention include N-(trimethoxysilylpropyl)ethylenediamine triacetic acid, trisodium salt, N-(triethoxysilylpropyl)ethylenediamine triacetic acid, trisodium salt, N-(trimethoxysilylpropyl) ethylenediamine triacetic acid, N-(trimethoxysilylpropyl) diethylenetriamine tetra acetic acid, N-(trimethoxysilylpropyl)amine diacetic acid, and metal-ion salts thereof.

It is preferred that substantially all (greater than 90%) of the metal-ion sequestraint is covalently bound to the nanoparticles, and is thus "anchored" to the nanoparticle. Metal-ion sequestraint that is not bound to the nanoparticles may dissolve and quickly diffuse through a system; and may be ineffective in removing metal-ions from the system. It is further preferred that the metal-ion sequestraint is present in an amount sufficient, or less than sufficient, to cover the surfaces of all nanoparticles. This is preferred because it maximizes the number of covalently bound metal-ion sequestraints, since once the surface of the nanoparticles is covered, no more covalent linkages to the nanoparticle may result.

The derivatized nanoparticles of the present invention may be prepared by general chemical synthetic methods. An aqueous or solvent based dispersion of the inorganic nanoparticles is prepared at a temperature below the boiling point of the mixture. To this dispersion, is then added the sequestraint having a chelating group and a functional group, which reacts with and forms a covalent bond to the surfaces of the inorganic nanoparticles. Alternatively, an intermediate may first be reacted with the nanoparticles and the intermediate subsequently reacted to form a metal-ion sequestraint.

The invention also provides an article comprising a polymeric layer, said polymeric layer further comprising immobilized derivatized nanoparticles (as described in detail above), comprising inorganic nanoparticles having an attached metal-ion sequestraint, wherein said inorganic nanoparticles have an average particle size of less than 200 nm and the derivatized nanoparticles have a stability constant greater than $10^{10}$ with iron (III). It is preferred that the polymeric layer is located on the surface(s) of the article. This is preferred because it provides the maximum contact between the polymeric layer and the surrounding environment. It is preferred that the polymeric layer is permeable to liquid media, and it is further preferred that the polymeric layer is permeable to aqueous media. This is preferred because permeability facilitates the contact of the contaminant metal-ions with the derivatized nanoparticles, which, in turn, facilitates the sequestration of the metal-ions at the nanoparticle surfaces.

It is preferred that the polymer has a water permeability of greater than $1000[(cm^3 \; cm)/(cm^2 \; sec/Pa)] \times 10^{13}$. It is further preferred that the polymer has a water permeability of greater than $5000[(cm^3 \; cm)/(cm^2 \; sec/Pa)] \times 10^{13}$. Preferred polymers for practice of the invention are one or more of polyvinyl alcohol, cellophane, water-based polyurethanes, polyester, nylon, high nitrile resins, polyethylene-polyvinyl alcohol copolymer, polystyrene, ethyl cellulose, cellulose acetate, cellulose nitrate, aqueous latexes, polyacrylic acid, polystyrene sulfonate, polyamide, polymethacrylate, polyethylene terephthalate, polystyrene, polyethylene, polypropylene or polyacrylonitrile or copolymers thereof. It is preferred that the polymeric layer has a thickness in the range of 0.1 microns to 10.0 microns. It is preferred that the derivatized nanoparticles are 0.1 to 50.0% by weight of the polymeric layer.

A support may be provided between the article and the polymeric layer. In this manner the composition of matter of the invention may be applied to the surfaces of a support by methods such as blade coating, dip coating, curtain and rod coating. The polymeric layer may also be applied by painting, spraying, casting, molding, blowing, extruding, etc. Supports suitable for practice of the invention are papers such as resin-coated paper, plain paper, coated paper, synthetic paper, melt-extrusion-coated paper, laminated paper, and polymeric supports such as cellulose derivatives, polyesters, polyethylene, polypropylene, mylar and poly ethylene terephthalate (PET).

In a preferred embodiment, the invention comprises a barrier layer; wherein the polymeric layer is between the surface of the article and the barrier layer and wherein the barrier layer does not contain the derivatized nanoparticles. The barrier layer may provide several functions including improving the physical strength and toughness of the article and resistance to scratching, marring, cracking, etc. However, the primary purpose of the barrier layer is to provide a barrier through which micro-organisms cannot pass. It is important to limit, or eliminate, the direct contact of micro-organisms with the surfaces of the derivatized nanoparticles, since many micro-organisms, under conditions of iron deficiency, may bio-synthesize molecules which are strong chelators for iron, and other metals. These bio-synthetic molecules are called "siderophores" and their primary purpose it to procure iron for the micro-organisms. Thus, if the microorganism are allowed to directly contact the derivatized nanoparticles of the invention, they may find a rich source of iron there, and begin to colonize directly at these surfaces. The siderophores produce by the micro-organisms may compete with the derivatized nanoparticles for the iron (or other bio-essential metal) at their surfaces. The barrier layer of the invention does not contain derivatized nanoparticles, and because micro-organisms are large, they may not pass or diffuse through the barrier layer. The barrier layer thus prevents contact of the micro-organisms with the polymeric layer containing the derivatized nanoparticles of the invention.

It is preferred that the barrier layer is permeable to liquid media. This is preferred because metal-ions in solution may then readily diffuse through the barrier layer and become sequestered in the underlying polymeric layer containing the derivatized nanoparticles. Thus, the barrier layer spatially separates the micro-organisms from the polymeric sequestration layer. It is preferred that the polymer(s) of the barrier layer has a water permeability of greater than $1000[(cm^3 \, cm)/(cm^2 \, sec/Pa)] \times 10^{13}$. It is further preferred that the polymer(s) of the barrier layer has a water permeability of greater than $5000[(cm^3 \, cm)/(cm^2 \, sec/Pa)] \times 10^{13}$. Preferred polymers for use in the barrier layer are one or more of polyvinyl alcohol, cellophane, water-based polyurethanes, polyester, nylon, high nitrile resins, polyethylene-polyvinyl alcohol copolymer, polystyrene, ethyl cellulose, cellulose acetate, cellulose nitrate, aqueous latexes, polyacrylic acid, polystyrene sulfonate, polyamide, polymethacrylate, polyethylene terephthalate, polystyrene, polyethylene, polypropylene, or polyacrylonitrile or copolymers thereof. It is preferred that the barrier layer has a thickness in the range of 0.1 microns to 10.0 microns.

The following examples are intended to illustrate, but not to limit the invention.

EXAMPLES

Preparation of Derivatized Nanoparticles:

Colloidal dispersions of silica particles were obtained from ONDEO Nalco Chemical Company. NALCO® 1130 had a median particle size of 8 nm, a pH of 10.0, a specific gravity of 1.21 g/ml, a surface area of about 375 m²/g, and a solids content of 30 weight percent. NALCO® 1140 had a median particle size of 11 nm, a pH of 9.7, a specific gravity of 1.29 g/ml, a surface area of about 200 m²/g, and a solids content of 40 weight percent. NALCO® 2329 had a median particle size of 75 nm, a pH of about 9.5, a specific gravity of 1.29 g/ml, a surface area of 40 m²/g, and a solids content of 40 weight percent. Boehmite (Aloha) was purchased from Sisal Inc. under the trade name Catapal 200®. N-(trimethoxysilylpropylethylenediamine triacetic acid, trisodium salt was purchased from Gelest Inc., 45% by weight in water. Electrophoretic mobility measurements were made using a Zeta-Meter System 3.0+ instrument (Zeta-Meter, Inc). Dispersions of the nanoparticles and derivatized nanoparticles (0.010 w/v %) were prepared using deionized distilled water. The pH was adjusted using 0.1M HCl or 0.1M KOH. The zeta potential (ζ) of the particles was computed as follows:

$$\zeta = (4\pi \eta u_E)/D$$

where n=the viscosity of the medium, $u_E$=electrophoretic mobility of the particle and D=the dielectric of the medium.

Derivatized nanoparticles A. To 267.00 g of silica NALCO® 1130 (30% solids) was added 200.00 g of distilled water and the contents mixed thoroughly using a mechanical mixer. To this suspension, was added 22.0 g of N-(trimethoxysilyl)propylethylenediamine triacetic acid, trisodium salt in 22.0 g distilled water with constant stirring at a rate of 5.00 ml/min. At the end of the addition the pH was adjusted to 7.1 with the addition of 4.04 g of glacial acetic acid, and the contents stirred for an hour at room temperature. Particle size analysis indicated an average particle size of 13 nm. The percent solids of the final dispersion was 17.3%.

Derivatized nanoparticles B. To 200.00 g of silica NALCO® 1140 (40% solids) was added 200.00 g of distilled water and the contents mixed thoroughly using a mechanical mixer. To this suspension, was added 22.0 g of N-(trimethoxysilyl)propylethylenediamine triacetic acid, trisodium salt in 22.0 g distilled water with constant stirring at a rate of 5.00 ml/min. At the end of the addition the pH was adjusted to 7.1 with the addition of 2.5 g of glacial acetic acid, and the contents stirred for an hour at room temperature. Particle size analysis indicated an average particle size of 20 nm. The percent solids of the final dispersion was 21.0%.

Derivatized nanoparticles C. Boehmite (AlOOH) 5.00 g was dispersed in 45.0 g distilled water to make a 10% by weight dispersion having an average particle size of 90 nm. The zeta potential of the AlOOH nanoparticles was found to be about +40 mV at a pH of about 4.0, indicating that the particles have a positive charge on their surfaces. To this suspension, with continuous stirring, was added 0.65 g of N-(trimethoxysilylpropylethylenediamine triacetic acid, trisodium salt, (45% in water). At the end of the addition, the pH was adjusted to 6.0 with the addition of 4 drops of glacial acetic acid, and the contents stirred for an hour at room temperature. Particle size analysis indicated an average particle size of 110 nm. The percent solids of the final dispersion was about 10.5%. The zeta potential of the derivatized nanoparticles was found to be about −35 mV at a pH of about 8.0, indicating that the particles were negatively charged. The change of the particle charge from positive (underivatized) to negative (derivatized) is an indication that the surface of the particles is modified with metal-ion sequestraint.

Preparation of Polymeric Layers of Derivatized Nanoparticles.

Coating 1. A coating solution was prepared as follows: 21.3 grams of the suspension of derivatized nanoparticles (B) above was combined with to 51.7 grams of pure distilled water and 26.5 g of a 40% solution of the polyurethane Permax 120 (Noveon Chemicals). 0.5 g of a 10% solution of the surfactant OLIN 10G was added as a coating aid. The mixture was then stirred and blade-coated onto a polymeric support using a 50 micron doctor blade. The coating was then dried at 40-50° C., to produce a clear transparent film having 2.2 g/m² of derivatized nanoparticles and 5.4 g/m² of polyurethane.

Coating 2. A coating solution was prepared as follows: 10.2 grams of the suspension of derivatized nanoparticles (A) above was combined with to 81.0 grams of pure distilled water and 8.8 g of a 40% solution of the polyurethane Permax 220 (Noveon Chemicals). The mixture was then stirred and blade-coated onto a polymeric support using a 150 micron doctor blade. The coating was then dried at 40-50° C., to produce a clear transparent film having 2.7 g/m² of derivatized nanoparticles and 5.4 g/m² of polyurethane.

Coating 3. A coating solution was prepared as follows: 10.2 grams of the suspension of derivatized nanoparticles (A) above was combined with to 15.7 grams of pure distilled water and 70.6 g of a 5% solution of polyvinyl alcohol. To the stirred mixture was then add 3.5 g of a 5% solution of glutaraldehyde to cross-link the polyvinyl alcohol. The mixture was then stirred and blade-coated onto a polymeric support using a 150 micron doctor blade. The coating was then dried at 40-50° C., to produce a clear transparent film having 2.7 g/m² of derivatized nanoparticles and 5.4 g/m² of polyvinyl alcohol.

Coating 4. A coating solution was prepared as follows: 10.2 grams of the suspension of derivatized nanoparticles (A) above was combined with to 81.0 grams of pure distilled water and 8.8 g of a 40% solution of the polyurethane R9699 (Avecia Chemicals). The mixture was then stirred and blade-coated onto a polymeric support using a 150 micron doctor blade. The coating was then dried at 40-50° C., to produce a clear transparent film having 2.7 g/m² of derivatized nanoparticles and 5.4 g/m² of polyurethane.

Sequestration of Iron from a Model Biological Environment.

Examples (1-4) and Comparison Examples C-1

A "model" biological liquid medium was prepared as follows: 12.5 g of sucrose, 12.5 g of glucose, 0.25 g of NaCl and 0.125 g of citric acid, and 2.0 ml of a 500 ppm solution of $Fe^{3+}$ were carefully dissolved in 498.0 ml of pure distilled water to produce a solution having: 5% sucrose, 5% glucose, 1000 ppm NaCl, 500 ppm citric acid and 2 ppm iron. 5 cm×5 cm pieces of the coatings prepared as described above were then contacted with 25.0 ml of the model biological liquid medium. The pieces of the coatings were left in contact with the medium for the time indicated in Table 2, and a 1.0 ml aliquot of the medium was taken for Fe analysis via inductively coupled plasma-atomic emission spectroscopy. A Comparison example was prepared using a 5 cm×5 cm piece of the polymeric support which did not contain a coating of the inventive composition. The data are given in Table 2.

TABLE 2

| Example or Comparison Example | coating solution | Concentration (ppm) Fe after 1d | Concentration (ppm) Fe after 2d |
|---|---|---|---|
| 1 | 1 | 0.212 | 0.16 |
| 2 | 2 | 0.36 | 0.12 |
| 3 | 3 | 0.30 | 0.10 |
| 4 | 4 | 0.16 | 0.10 |
| C-1 | none | 1.94 | 2.04 |

The data of Table 2 indicate that the inventive coatings are able to sequester iron from a liquid medium, and able to sequester iron from a liquid medium containing representative biological compounds. The comparison example shows no reduction of iron after two days exposure. In some cases as much as 95% of the free iron is removed from the model biological liquid medium, and the level of iron contamination is reduced to as low as 100 ppb (0.1 ppm).

The invention has been described in detail with particular reference to the preferred embodiments thereof, but it will be understood that variations and modifications can be effected within the scope of the invention.

The invention claimed is:

1. An article comprising a polymeric layer, said polymeric layer further comprising immobilized derivatized nanoparticles comprising inorganic nanoparticles having an attached metal-ion sequestraint, wherein said inorganic nanoparticles have an average particle size of less than 200 nm and the metal-ion sequestraint comprises an alpha amino carboxylate, a hydroxamate, or a catechol functional group, further comprising a barrier layer; wherein the polymeric layer is between the surface of the article and the barrier layer and wherein the barrier layer does not contain the derivatized nanoparticles.

2. The article of claim 1 wherein the derivatized nanoparticles are 0.1 to 50.0% by weight of the polymeric layer.

3. The article of claim 1 wherein said inorganic nanoparticles comprise silica oxides, alumina oxides, boehmites, titanium oxides, zinc oxides, tin oxides, zirconium oxides, yttrium oxides, hafnium oxides, clays, or alumina silicates.

4. The article of claim 3 wherein said inorganic nanoparticles comprise silicon dioxide, alumina oxide, clays or boehmite.

5. The article of claim 1 wherein the metal-ion sequestraint is attached to the nanoparticle, by reacting the nanoparticle with a metal alkoxide intermediate of the sequestraint having the general formula:

$$M(OR)_{4-x}R'_x;$$

wherein M is silicon, titanium, aluminum, tin, or germanium;

x is an integer from 1 to 3;

R is an organic group; and

R' is an organic group containing an alpha amino carboxylate, a hydroxamate, or a catechol.

6. The article of claim 1 wherein said metal-ion sequestraint is attached to the nanoparticle by reacting the nanoparticle with a silicon alkoxide intermediate of the sequestraint having the general formula:

$$Si(OR)_{4-x}R'_x;$$

wherein x is an integer from 1 to 3;

R is an alkyl group; and

R' is an organic group containing an alpha amino carboxylate, a hydroxamate, or a catechol.

7. The article of claim 1 wherein substantially all the metal-ion sequestraint is covalently bound to the nanoparticles.

8. The article of claim 1 wherein the polymeric layer is permeable to liquid media.

9. The article of claim 1 wherein the polymeric layer is permeable to aqueous media.

10. The article of claim 9 wherein the polymeric layer has a water permeability of greater than $1000[(cm^3\ cm)/(cm^2\ sec/Pa)] \times 10^{13}$.

11. The article of claim 9 wherein the polymeric layer has a water permeability of greater than $5000[(cm^3\ cm)/(cm^2\ sec/Pa)] \times 10^{13}$.

12. The article of claim 1 wherein the polymeric layer comprises one or more of polyvinyl alcohol, cellophane, water-base polyurethanes, polyester, nylon, high nitrile resins, polyethylene-polyvinyl alcohol copolymer, polystyrene, ethyl cellulose, cellulose acetate, cellulose nitrate, aqueous latexes, polyacrylic acid, polystyrene sulfonate, polyamide, polymethacrylate, polyethylene terephthalate, polystyrene, polyethylene, polypropylene or polyacrylonitrile, or copolymers thereof.

13. The article of claim 1 wherein the baffler layer is permeable to liquid media.

14. The article of claim 1 wherein the barrier layer is permeable to aqueous media.

15. The article of claim 14 wherein the baffler layer has a water permeability of greater than $1000[(cm^3\ cm)/(cm^2\ sec/Pa)] \times 10^{13}$.

16. The article of claim 14 wherein the baffler layer has a water permeability of greater than $5000[(cm^3\ cm)/(cm^2\ sec/Pa)] \times 10^{13}$.

17. The article of claim 1 wherein the barrier layer has a thickness in the range of 0.1 microns to 10 microns.

18. The article of claim 1 wherein the baffler layer comprises one or more of polyvinyl alcohol, cellophane, water-based polyurethanes, polyester, nylon, high nitrile resins, polyethylene-polyvinyl alcohol copolymer, polystyrene, ethyl cellulose, cellulose acetate, cellulose nitrate, aqueous latexes, polyacrylic acid, polystyrene sulfonate, polyamide, polymethacrylate, polyethylene terephthalate, polystyrene, polyethylene, polypropylene or polyacrylonitrile, or copolymers thereof.

19. The article of claim 1 wherein the barrier layer prevents the diffusion or passage of micro-organisms.

20. The article of claim 1 wherein the barrier layer has a greater water permeability than the polymeric layer.

21. The article of claim 1 wherein said inorganic nanoparticles have an average particle size of less than 100 nm.

22. The article of claim 1 wherein said inorganic nanoparticles have an average particle size of less than 20 nm.

23. The article of claim 1 wherein said inorganic nanoparticles have a specific surface area of greater than 300 $m^2/g$.

24. The article of claim 1 wherein said inorganic nanoparticles have a specific surface area of greater than 100 $m^2/g$.

25. The article of claim 1 wherein said inorganic nanoparticles have a specific surface area of greater than 200 $m^2/g$.

26. The article of claim 1 wherein said inorganic nanoparticles have a specific surface area of greater than 300 $m^2/g$.

27. The article of claim 1 wherein greater than 95% by weight of the inorganic nanoparticles have a particle size of less than 200 nm.

28. The article of claim 1 wherein greater than 95% by weight of the inorganic nanoparticles have a particle size of less than 50 nm.

* * * * *